United States Patent [19]

Scanlon

[11] Patent Number: 5,819,918
[45] Date of Patent: *Oct. 13, 1998

[54] RETAINER PACKAGE FOR RESILIENT FILAMENTS

[75] Inventor: Christopher Scanlon, Milford, Conn.

[73] Assignee: United States Surgical Corporation, Norwalk, Conn.

[*] Notice: The portion of the term of this patent subsequent to Dec. 8, 2015, has been disclaimed.

[21] Appl. No.: 709,962

[22] Filed: Sep. 9, 1996

Related U.S. Application Data

[63] Continuation of Ser. No. 567,182, Dec. 8, 1995, Pat. No. 5,560,477, which is a continuation of Ser. No. 120,201, Sep. 13, 1993, abandoned.

[51] Int. Cl.⁶ ............................................ A61B 17/06
[52] U.S. Cl. .......................... 206/63.3; 206/382
[58] Field of Search .................. 206/63.3, 380, 206/382, 383, 314; 53/473, 452, 475

[56] References Cited

U.S. PATENT DOCUMENTS

| | | |
|---|---|---|
| D. 263,505 | 3/1982 | Black . |
| D. 272,600 | 2/1984 | Kubas . |
| 2,692,676 | 10/1954 | Grover . |
| 3,062,372 | 11/1962 | Egler et al. . |
| 3,127,992 | 4/1964 | Horine . |
| 3,136,418 | 6/1964 | Stacy et al. . |
| 3,162,307 | 12/1964 | Regan, Jr. . |
| 3,167,895 | 2/1965 | Egler et al. . |
| 3,185,299 | 5/1965 | Trainer . |
| 3,206,018 | 9/1965 | Lewis et al. . |
| 3,280,971 | 10/1966 | Regan, Jr. . |
| 3,338,401 | 8/1967 | Regan, Jr. . |
| 3,357,550 | 12/1967 | Holmes et al. . |
| 3,363,751 | 1/1968 | Shave et al. . |
| 3,444,994 | 5/1969 | Kaepernik et al. . |
| 3,487,917 | 1/1970 | Shave et al. . |
| 3,545,608 | 12/1970 | Berger et al. . |
| 3,627,120 | 12/1971 | Bordeau . |
| 3,651,935 | 3/1972 | Nysten . |
| 3,731,793 | 5/1973 | Hagel . |
| 3,759,376 | 9/1973 | Lisowski . |
| 3,779,375 | 12/1973 | Foster . |
| 3,857,484 | 12/1974 | Thyen . |
| 3,869,044 | 3/1975 | Olssen et al. . |
| 3,876,068 | 4/1975 | Sonnino . |
| 3,939,969 | 2/1976 | Miller . |
| 3,959,947 | 6/1976 | Sonnino . |
| 3,972,418 | 8/1976 | Schuler et al. . |
| 3,985,227 | 10/1976 | Thyen et al. . |
| 4,014,434 | 3/1977 | Thyen . |
| 4,034,850 | 7/1977 | Mandel et al. . |

(List continued on next page.)

FOREIGN PATENT DOCUMENTS

| | | |
|---|---|---|
| 662417 | 4/1963 | Canada . |
| 0505612 | 9/1992 | European Pat. Off. . |
| 8631420 | 1/1987 | Germany . |
| 680089 | 10/1952 | United Kingdom . |
| 2161130 | 1/1986 | United Kingdom . |

*Primary Examiner*—Jacob K. Ackun

[57] ABSTRACT

A resilient filament retaining package includes a plurality of panel members foldably connected to each other along transverse sides thereof and arranged to fold upon each other to form a plurality of superposed compartments defined between pairs of adjacent panel members. Each compartment is dimensioned to contain at least one flexible resilient filament portion therein in a coiled configuration. Receiving port apertures are provided in the forward panel member of each compartment and are intended to assist in loading individual filament portions in each compartment. The apertures are in general concentric alignment with each other such that each compartment may be accessed for loading purposes from a front side of the folded retainer package. A backing panel having a needle securing park may be attached to the folded package. A method for loading the package is also disclosed. The package can be particularly useful for retaining surgical sutures.

5 Claims, 10 Drawing Sheets

5,819,918
Page 2

U.S. PATENT DOCUMENTS

| | | |
|---|---|---|
| 4,063,638 | 12/1977 | Marwood . |
| 4,069,912 | 1/1978 | Black et al. . |
| 4,120,395 | 10/1978 | Mandel et al. . |
| 4,121,711 | 10/1978 | Bolanowski . |
| 4,126,221 | 11/1978 | Cerwin . |
| 4,135,623 | 1/1979 | Thyen . |
| 4,142,628 | 3/1979 | Marocco et al. . |
| 4,183,431 | 1/1980 | Schmidt et al. . |
| 4,235,563 | 11/1980 | Komarnycky . |
| 4,249,656 | 2/1981 | Cerwin et al. . |
| 4,284,194 | 8/1981 | Flatau . |
| 4,369,880 | 1/1983 | Giggey et al. . |
| 4,391,365 | 7/1983 | Batchelor . |
| 4,406,363 | 9/1983 | Aday . |
| 4,412,613 | 11/1983 | Kubas . |
| 4,412,614 | 11/1983 | Ivanov et al. . |
| 4,413,727 | 11/1983 | Cerwin et al. . |
| 4,424,898 | 1/1984 | Thyen et al. ............................ 206/63.3 |
| 4,427,109 | 1/1984 | Roshdy . |
| 4,483,437 | 11/1984 | Cerwin et al. . |
| 4,496,045 | 1/1985 | Ferguson et al. . |
| 4,549,649 | 10/1985 | Roshdy . |
| 4,555,016 | 11/1985 | Aday et al. . |
| 4,572,363 | 2/1986 | Alpern . |
| 4,574,948 | 3/1986 | Huck et al. . |
| 4,574,957 | 3/1986 | Stead . |
| 4,615,435 | 10/1986 | Alpern et al. . |
| 4,699,271 | 10/1987 | Lincoln et al. . |
| 4,700,833 | 10/1987 | Smith . |
| 4,708,241 | 11/1987 | Black . |
| 4,813,537 | 3/1989 | Okuhara et al. . |
| 4,884,681 | 12/1989 | Roshdy et al. . |
| 4,896,767 | 1/1990 | Pinheiro . |
| 4,946,043 | 8/1990 | Roshdy et al. . |
| 5,048,678 | 9/1991 | Chambers . |
| 5,277,299 | 1/1994 | Holzwarth et al. ..................... 206/63.3 |
| 5,301,801 | 4/1994 | Sinn ....................... 206/63.3 |
| 5,560,477 | 10/1996 | Scanlon ................... 206/63.3 |

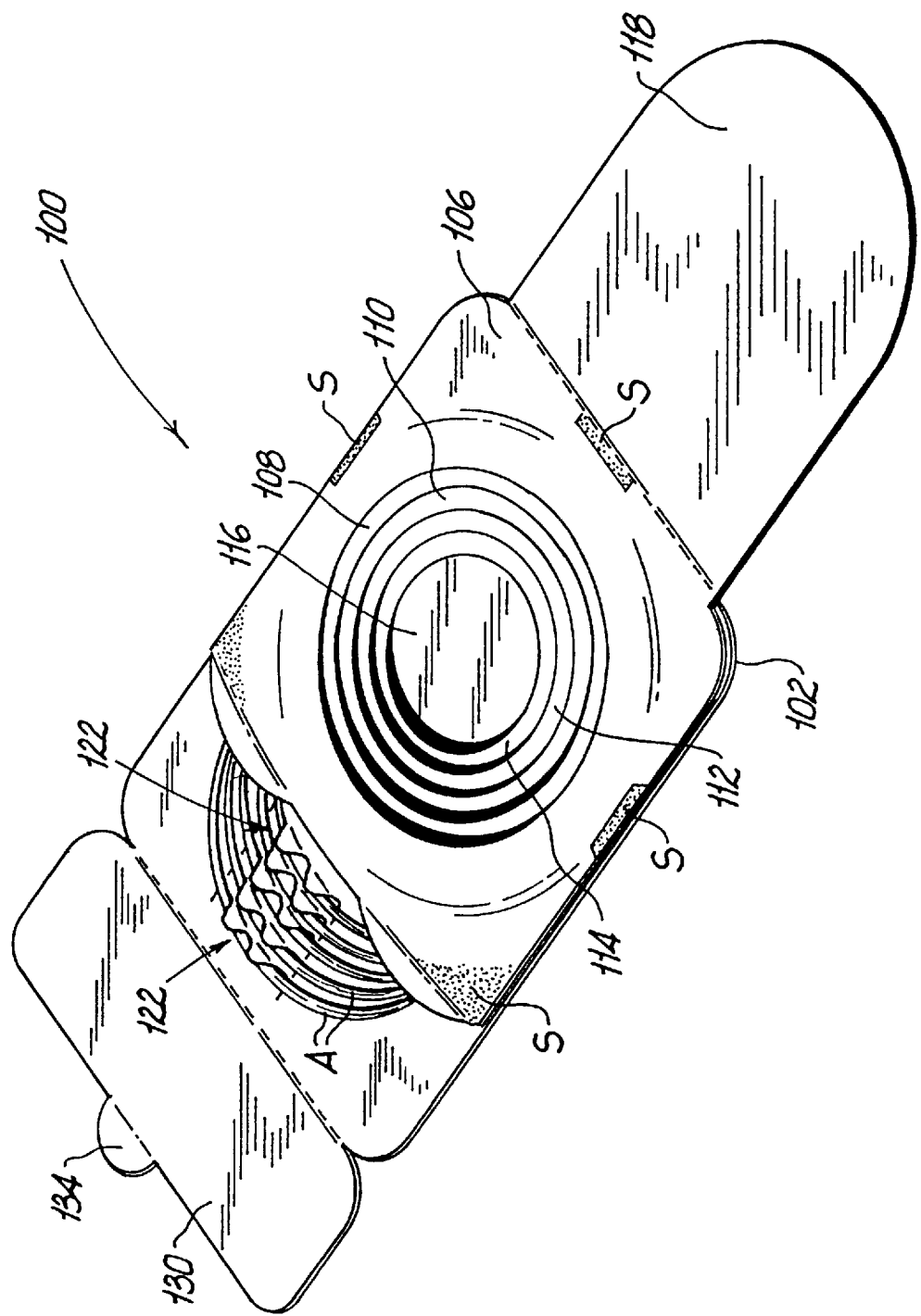

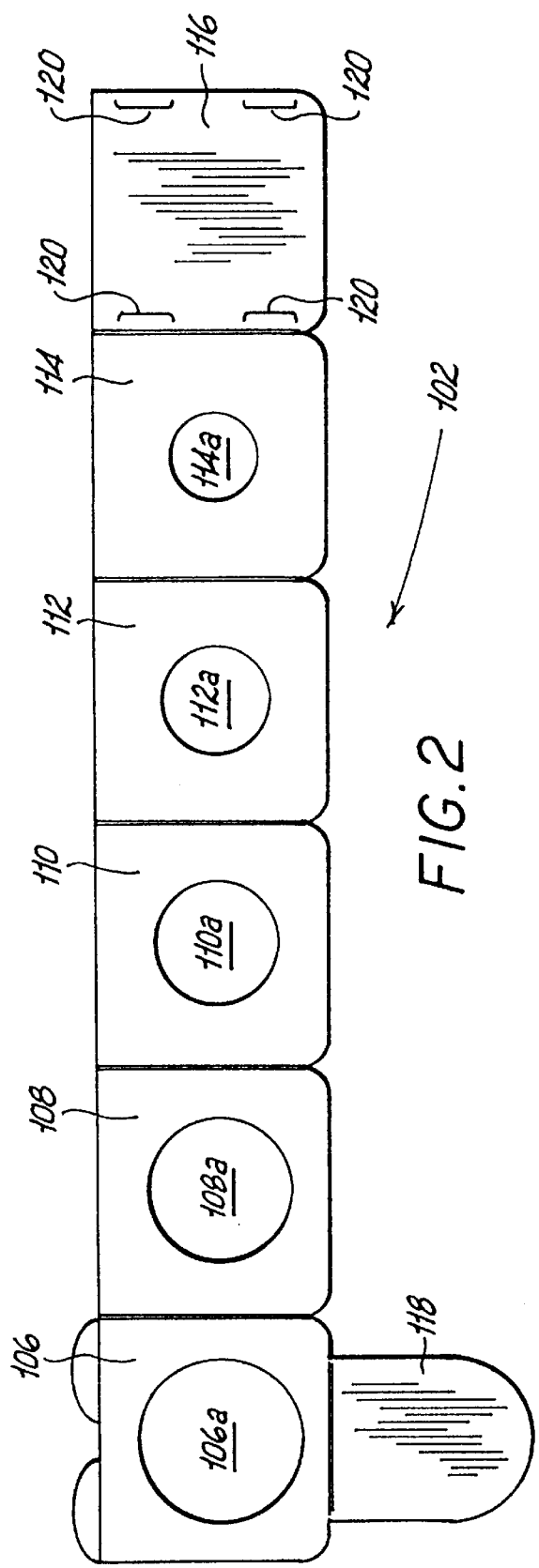
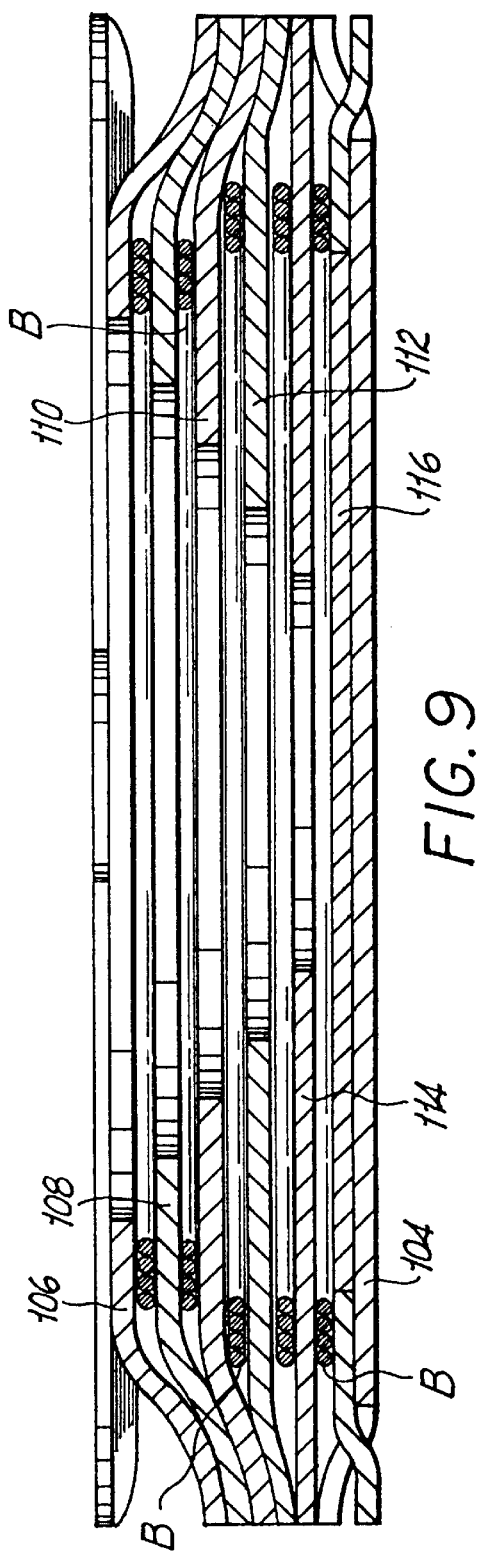

RETAINER PACKAGE FOR RESILIENT FILAMENTS

This is a continuation of U.S. application Ser. No. 08/567,182 filed Dec. 8, 1995, now U.S. Pat. No. 5,560,477, which is a continuation of U.S. application Ser. No. 08/120, 201 filed Sep. 13, 1993 and now abandoned.

BACKGROUND OF THE INVENTION

1. Field of the Invention

The invention relates to a new and useful retainer package for resilient filaments and more particularly to a package for retaining at least one resilient surgical suture in a manner for ready-removal.

2. Description of the Related Art

Many surgical sutures possess certain mechanical characteristics such as stiffness and a tendency to be wire-like and resilient. In the past, such sutures have been retained in packages having interconnected panel members. Typically, the suture is wound in a figure-eight or coiled configuration about winding projections which extend through apertures formed in one of the panels of the package. The remaining panels of the package are then folded onto the suture to enclose the suture within the package. A disadvantage with these methods is that the sutures can be damaged during loading and/or storage. In the figure-eight configuration, for example, kinking and wearing can occur where the sutures cross over. When using winding projections, for example, the sutures can be damaged by stress when being wound.

The aforedescribed packages for retaining a surgical suture have also failed to take advantage of the resilient qualities of certain suture materials to aid in the loading of the package. In particular, it has been found that a surgical suture having resilient characteristics such as catgut or some of the synthetic suture products including polypropylene and polyester may be inserted or fed into an opening in the package in a manner such that during insertion the suture naturally assumes a coiled configuration within the package.

Accordingly, there is a need for suture retainers which reduce or prevent damage to sutures during loading and/or storage. There is also a need for suture retainers with internal cavities or retaining areas, which do not necessitate the utilization of winding projections around which sutures must be wound to be loaded. There is also a need for suture retainers which are adapted to store sutures in a configuration which avoids or reduces cross-over points. It is also desirable to provide a package which is substantially fully assembled prior to loading. There is also a need for filament packaging capable of storing and maintaining filaments in some form of spaced relation to each other so that access and removal of the filaments may be readily available without adversely affecting the filament.

SUMMARY OF THE INVENTION

The present invention provides a retainer package for storing a plurality of resilient filaments, i.e., surgical sutures. The package comprises a plurality of panel members foldably connected to each other along transverse sides thereof. The panel members are arranged to fold upon each other to form a plurality of superposed compartments defined between pairs of adjacent panel members. Each compartment is dimensioned to contain at least one flexible resilient filament portion therein in a coiled configuration. The package further comprises receiving port means associated with each compartment for loading at least one coiled flexible resilient filament in each compartment.

In a preferred embodiment, the package is adapted to retain surgical sutures. The suture receiving port means comprises an aperture formed in a forward panel member of each suture compartment. Preferably, the suture loading apertures of each suture compartment are in general concentric alignment with each other such that each suture compartment may be accessed for suture loading purposes from a front side of the retainer package when the panel members are in their folded condition. It is further preferable that the suture loading apertures of the suture compartments incrementally decrease in diameter from a front most suture compartment to a rear most suture compartment to facilitate access to the compartments.

The retainer package of the present invention can further comprise a backing panel which may be secured to the rear panel member of the rearmost suture compartment. If armed sutures are being loaded, the backing panel can comprise means for securing surgical needles attached to the individual suture portions. A preferred needle securing means comprises portions cut out and lifted from the plane defined by the backing panel. Respective pluralities of cut portions can be dimensioned and positioned to engage respective portions of the suture needles to releasably secure the needles in respective fixed positions. In an alternative embodiment, the needle securing means comprises a foam park having slits configured and dimensioned to accommodate the needles.

A needle protecting panel member foldably attached to an upper edge of the backing panel can also be provided. The needle protecting panel can be adapted to fold onto the needles secured within the needle securing means and can include a tab member at an upper edge thereof, which is engagable with an upper edge of one of suture panel members to retain the needle protecting panel in a folded condition.

The suture retainer can further comprise an aperture panel member attached to one of the suture panels and adapted to fold onto the folded suture panels to at least partially cover the suture loading apertures of each suture compartment.

The present invention is also directed to a method for loading surgical sutures into a retainer package, comprising the steps of providing a plurality of suture panel members foldably connected to each other along transverse sides thereof and arranged to fold upon each other to form a plurality of superposed suture compartments defined between pairs of adjacent panel members, folding the suture panel members to form the plurality of superposed suture compartments, introducing at least one suture portion into an aperture formed in a forward panel member of a suture compartment and feeding the suture portion into the suture compartment to load the suture portion. If multiple sutures are to be loaded, i.e., one in each suture compartment, at least a portion of the sutures can be individually positioned into their respective compartments utilizing their respective loading apertures. Subsequent to positioning, the sutures can be individually or simultaneously caused to assume a coiled configuration in their respective compartments by forcing the sutures into the retainer.

BRIEF DESCRIPTION OF THE DRAWING(S)

Preferred embodiments of the invention will be described hereinbelow with reference to the drawings wherein:

FIG. 1 is a perspective view of the suture retainer package constructed according with the present invention;

FIG. 2 is a plan view of a blank sheet of the retainer package of FIG. 1 defining a plurality of panel members foldably connected to each other;

FIG. 9 is a cross-sectional view taken along the lines 9—9 of FIG. 7 illustrating the individual sutures stored within the suture compartments;

Figure 15:
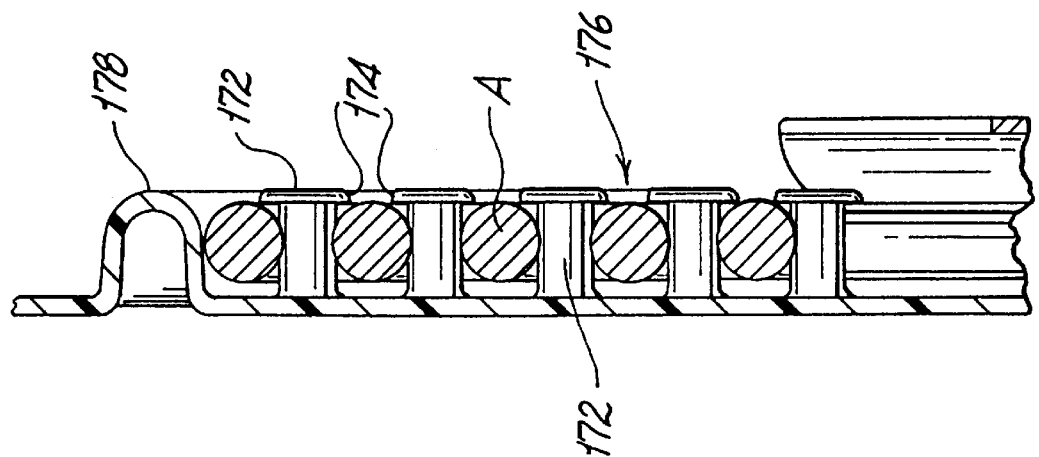
Figure 14:
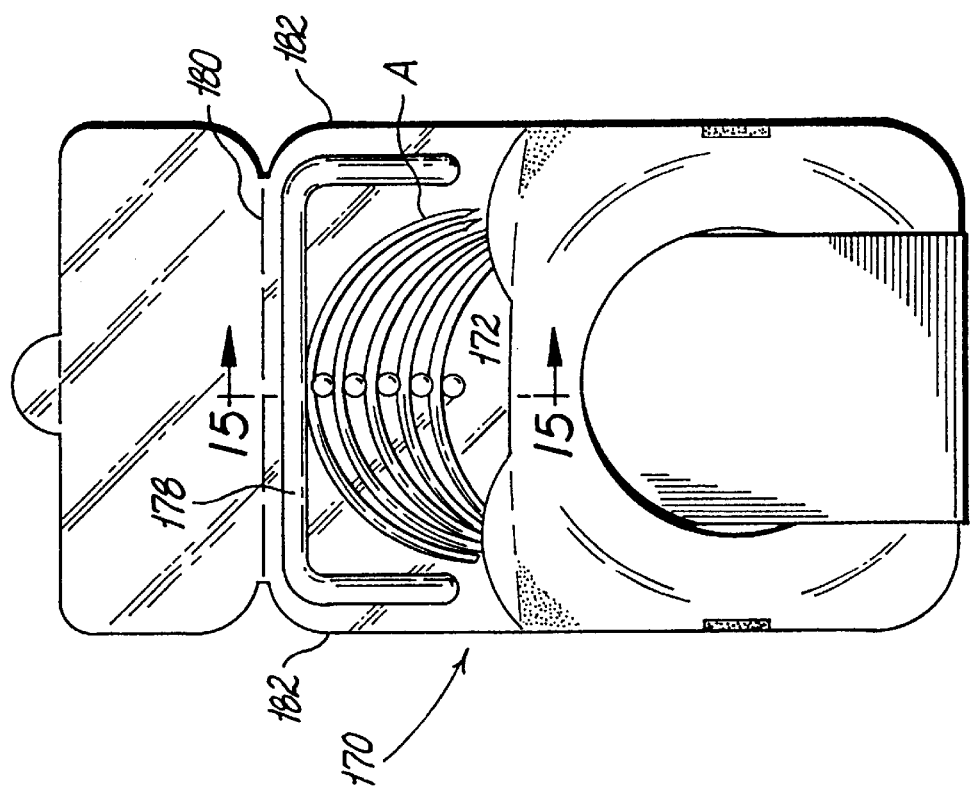

FIG. 14 is a frontal plan view of an alternative embodiment of the suture package of FIG. 1 including a molded plastic backing panel having a plurality of adjacent arcuate raised portions with peripheral lip portions for securing the needles; and FIG. 15 is a cross-sectional view taken along the lines 15—15 of FIG. 14 illustrating retention of the needles within needle receiving slots defined by the adjacent raised portion and peripheral lip portions.

DESCRIPTION OF THE PREFERRED EMBODIMENT(S)

Figure 3:
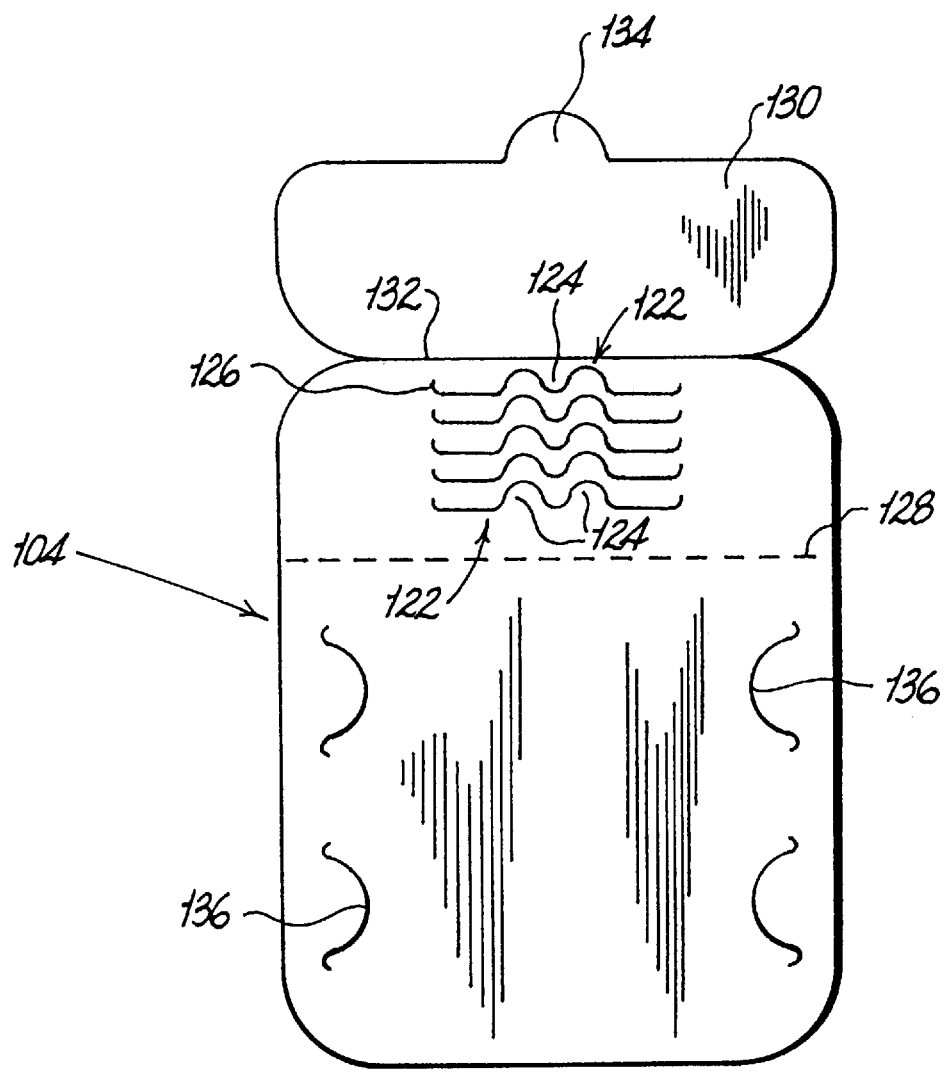
FIG. 3 is a plan view of the backing panel of the package of FIG. 1 illustrating needle holding tabs for securing needles.

Referring now to FIGS. 1–3, there is illustrated the suture package 100 constructed in accordance with the present invention. FIG. 1 illustrates the package 100 in an assembled condition. FIG. 2 is a plan view of a blank sheet 102 of package 100 defining a row of panel members foldably connected to each other and adapted to fold onto each other to form suture compartments. FIG. 3 is a plan view of a backing panel 104 of suture package 100. When the blank sheet 102 is folded to form the suture compartments and securely positioned on the backing panel 104, the suture package will appear as shown in FIG. 1.

Referring once again to FIG. 2, the blank sheet 102 is illustrated and includes a row of separate and individual generally rectangular panels 106, 108, 110, 112, 114 and 116 connected to each other along respective transverse sides as shown. Panels 106–116 are adapted to fold onto each other in the manner shown in FIG. 4 to form a plurality of superposed suture compartments. Each compartment is dimensioned to retain at least one suture in a coiled configuration.

Panels 106, 108, 110, 112 and 114 include circular apertures 106a, 108a, 110a, 112a and 114a, respectively. Apertures 106a–114a serve as suture loading ports to provide access to the suture compartments formed by the folded blank sheet 102 and to assist in loading the compartments with sutures. The apertures 106a–114a share a common central axis to provide the concentric arrangement shown in FIG. 1. In a preferred embodiment, the diameters of the apertures incrementally decrease from panel 106 to panel 114, the importance of which will be appreciated from the description below.

Figure 4:
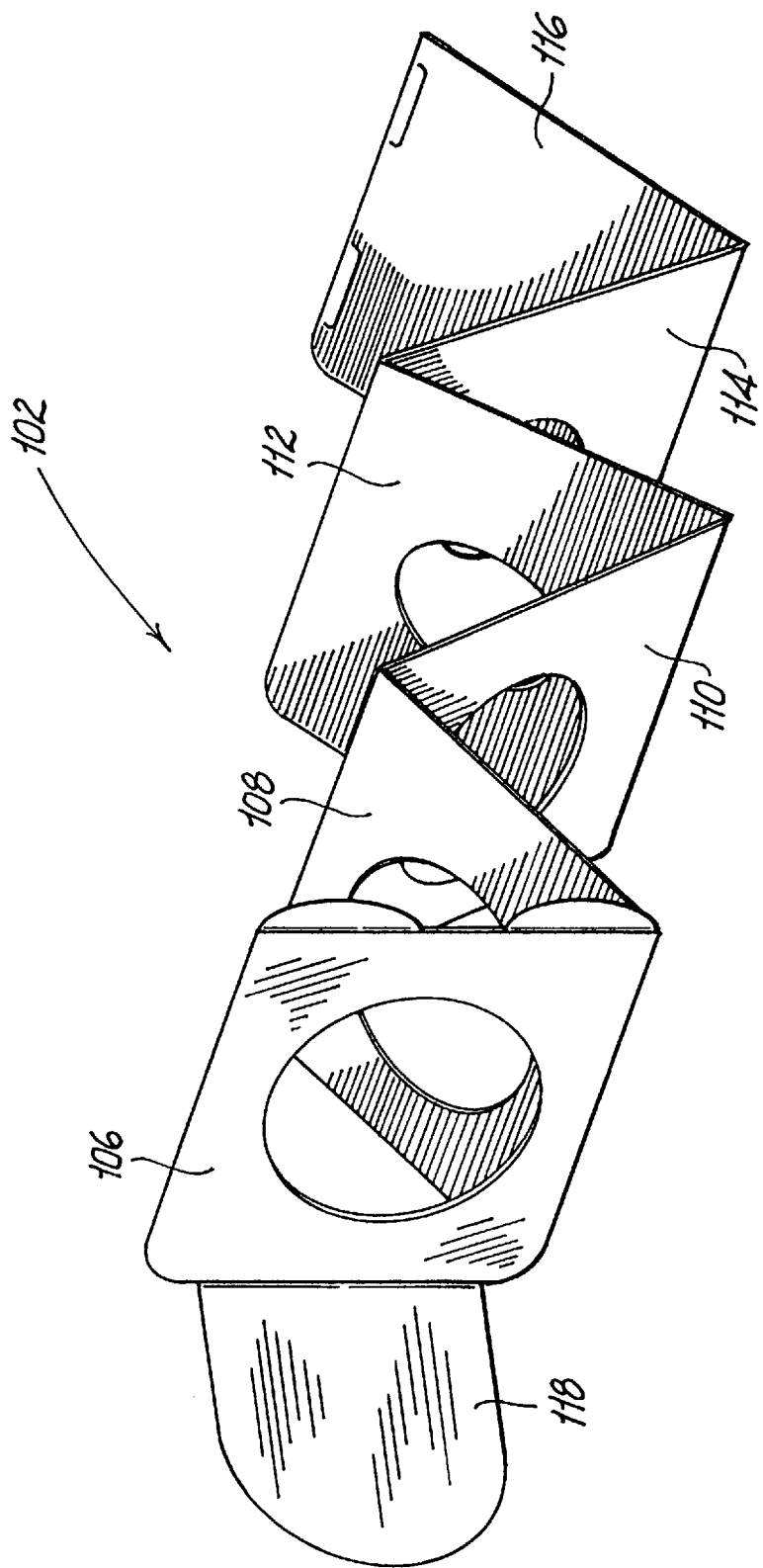
FIG. 4 is a perspective view of the blank sheet of FIG. 2 illustrating a sequence of folding the panel members to form individual suture compartments.

As shown in FIG. 1 taken in conjunction with FIG. 4, in the folded condition of blank sheet 102, five superposed suture compartments are formed between adjacent panel members. The front most compartment defined between folded panels 106, 108 has aperture 106a serving as its suture loading port. The next adjacent or second compartment formed between panels 108, 110 has aperture 108a as its suture loading port. The third compartment defined by panels 110, 112 has aperture 110a as its suture loading port while the fourth compartment has aperture 112a as the loading port. The rear most compartment defined between panels 114, 116 has aperture 114a as its suture loading port. As shown in the FIGS., the concentric arrangement of apertures 106a–114a and the respective dimensioning of the apertures, i.e., the incremental decrease in the diameters of the suture ports 106a–114a going from the front of the folded sheet 102 to the rear of the folded sheet 102, permit each suture compartment to be readily accessed from the front side of the package. Accordingly, each compartment may be loaded by inserting a suture in the front side of the package, positioning the suture within the desired loading aperture corresponding to the targeted suture compartment and feeding the suture, either manually or by automation, into the respective suture compartment such that the suture assumes a coiled configuration within the compartment and is enclosed within the suture panels defining the compartment. The preferred loading sequence will be described in greater detail hereinbelow.

Referring again to FIG. 2, an aperture panel 118 is foldably attached to a lower edge of panel 106. Aperture panel 118 folds onto panel 106 when sheet 102 is in the folded condition to cover the panel apertures and enclose the loaded sutures. Panel 116 of sheet 102 includes four slits 120 disposed on the peripheral edges thereof. Slits 120 assist in securing backing panel 104 to folded sheet 102 to form the suture package shown in FIG. 1. Clearly, one skilled in the art can devise other methods to secure backing panel 104 to sheet 102 and the present invention is not limited to the detailed embodiments discussed herein.

Sheet 102 may be fabricated from paperboard, fiberboard or any other fibrous material such as Tyvek® (available from Du Pont). Sheet 102 is preferably die cut to form the series of interconnected panels and apertures.

Referring now to FIG. 3, in conjunction with FIG. 1, backing panel 104 is preferably formed from a single sheet of suitable material, e.g., stiff paper or paperboard, plastics, laminates and the like which is die cut to provide the desired configuration. A preferred material for backing panel 104 is 0.005 lb. Monadnock paper available from Monadnock Paper Mills, Inc., Bennington, N.H. Backing panel 104 includes five series of sinusoidal cuts 122 formed in an upper portion of the panel. Sinusoidal cuts 122 define alternating tabs 124 which are respectively positioned to be lifted so as to receive and retain curved suture needles A (FIG. 1). Each end of a sinusoidal cut terminates in an arcuate slit portion 126 (FIG. 3). Arcuate slit portions 126 permit relaxation of the material defining the sinusoidal cuts to more effectively accommodate the loaded needles A and to reduce the stress placed on the material.

Figure 7:
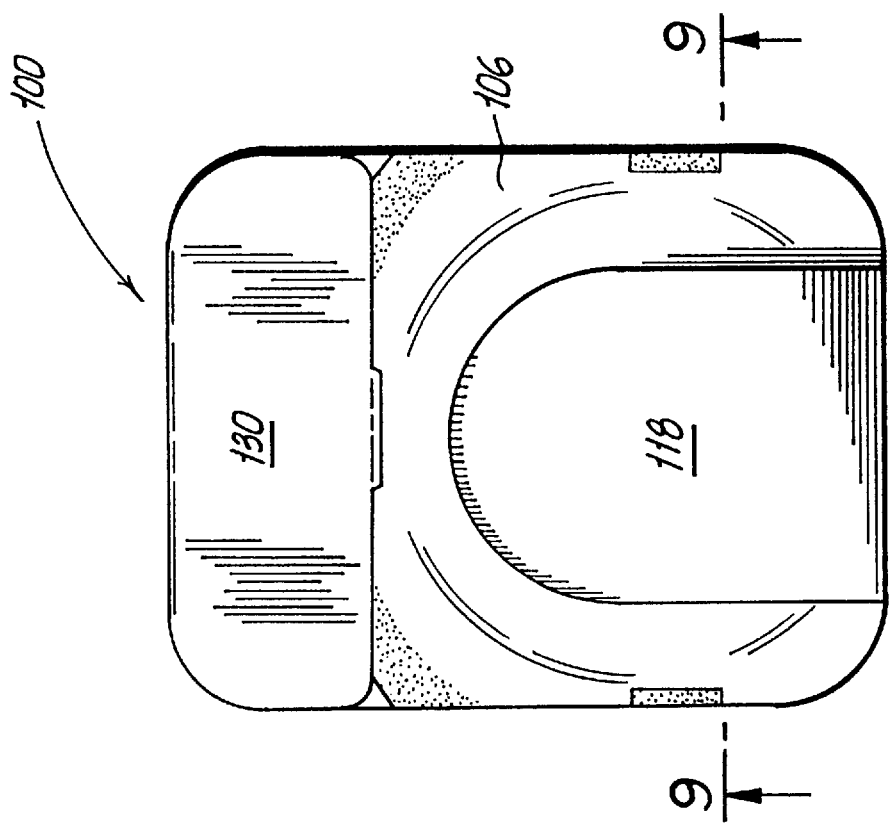
FIG. 7 is a frontal plan view of the retainer package of FIG. 1 illustrating a secured position of the needle protecting flap and aperture cover panel of the retainer package.

Backing panel 104 includes a lateral perforated score line 128 (FIG. 3) disposed beneath the sinusoidal cuts 122. Score line 128 permits the upper needle retaining portion of the backing panel 104 to fold back upon itself to facilitate removal of needles A. A needle protecting flap 130 is connected to the upper portion of backing panel 104 along score line 132. Protecting flap 130 folds along score line 132 to cover and protect the needles retained within the series of sinusoidal cuts 122. An arcuate locking tab 134 is disposed along the upper edge of protecting flap 130. Locking tab 134 engages an upper edge of one of the panel members of sheet 102 to retain protecting flap 130 in the folded condition as best shown in FIG. 7.

Figure 8:
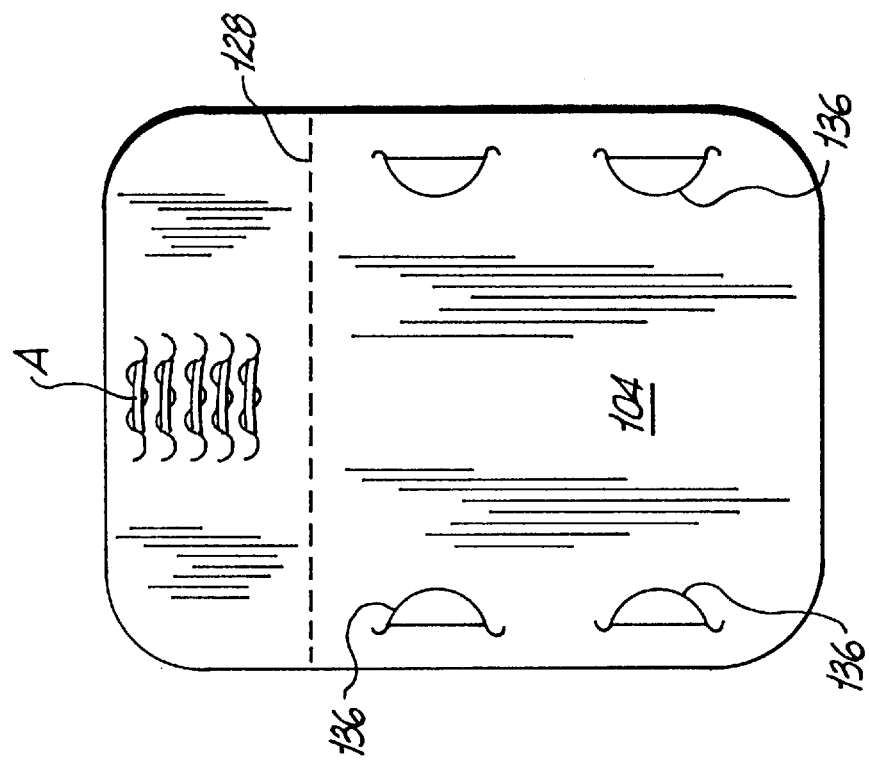
FIG. 8 is a rear plan view of the retainer package of FIG. 1 illustrating locking engagement of respective slots and tabs of the fully folded blank sheet and the backing panel to secure the folded blank sheet to the backing panel.

Referring again to FIG. 3, backing panel 104 includes four tabs 136 of generally arcuate shape positioned at respective corners of the panel. Tabs 136 are dimensioned to be received within correspondingly positioned and dimensioned slots 120 (FIG. 2) formed in panel 116 of sheet 102 to secure the backing panel 104 to the folded sheet 102. FIG. 8 illustrates the corresponding engagement of tabs 136 of backing panel 104 and slits 120 of panel 116 in more detail.

Package 100 is intended to store a plurality of resilient filaments, i.e., sutures, in a generally coiled configuration. The package 100 is particularly contemplated to accommodate sutures having resilient characteristics such as catgut, steel, polypropylene, polyester, Dacron™ or the like. It is also to be appreciated that package 100 can accommodate sutures fabricated from cotton, silk, linen and absorbable materials such as polymers and copolymer of glycolic and lactic acids. Additionally, package 100 can be used to accommodate filaments other than sutures, i.e., strings for musical instruments, fishing lines, etc.

Figure 5:
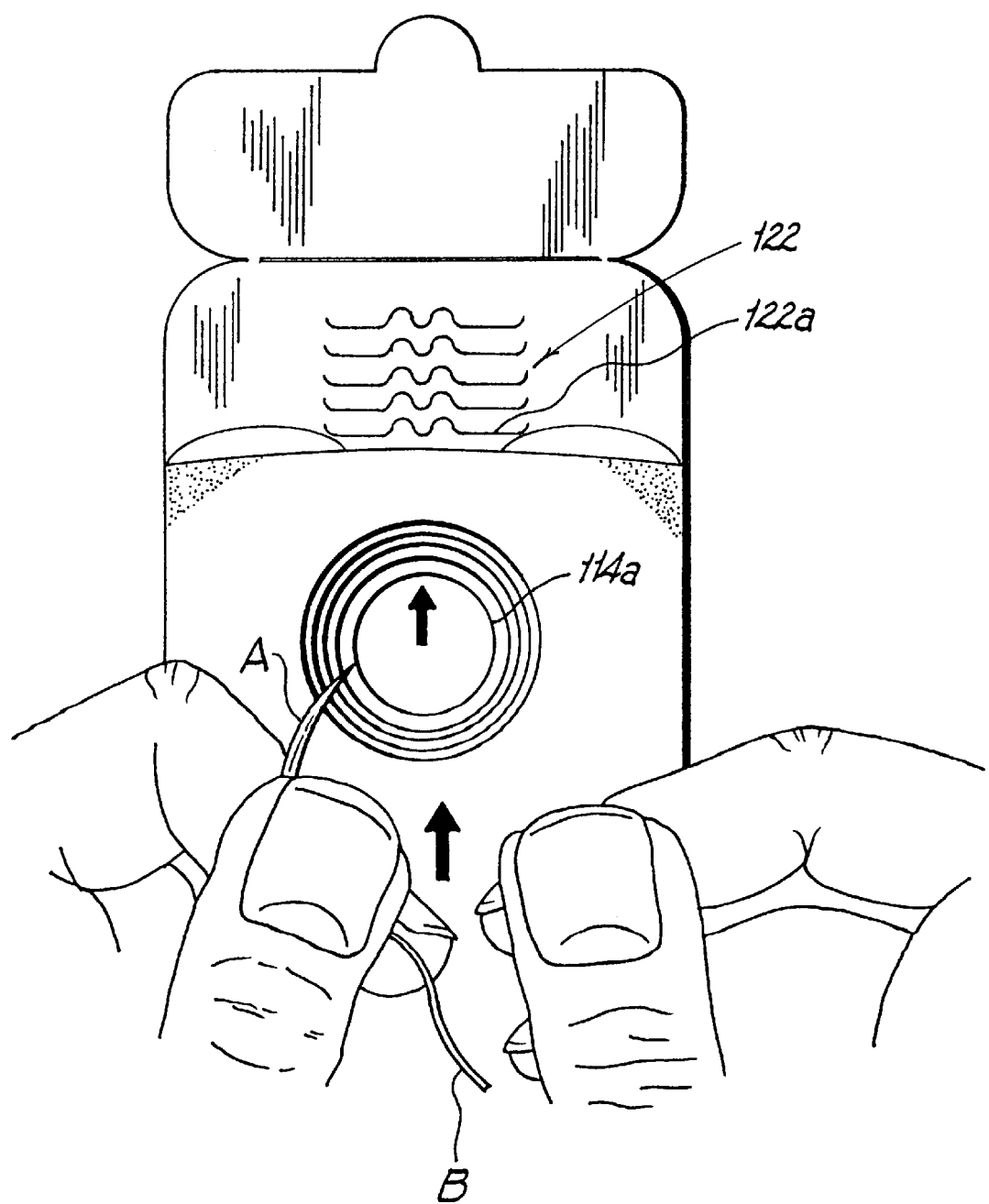
FIGS. 5–6 illustrate a sequence of steps for loading resilient sutures into the individual suture compartments.
Figure 6:
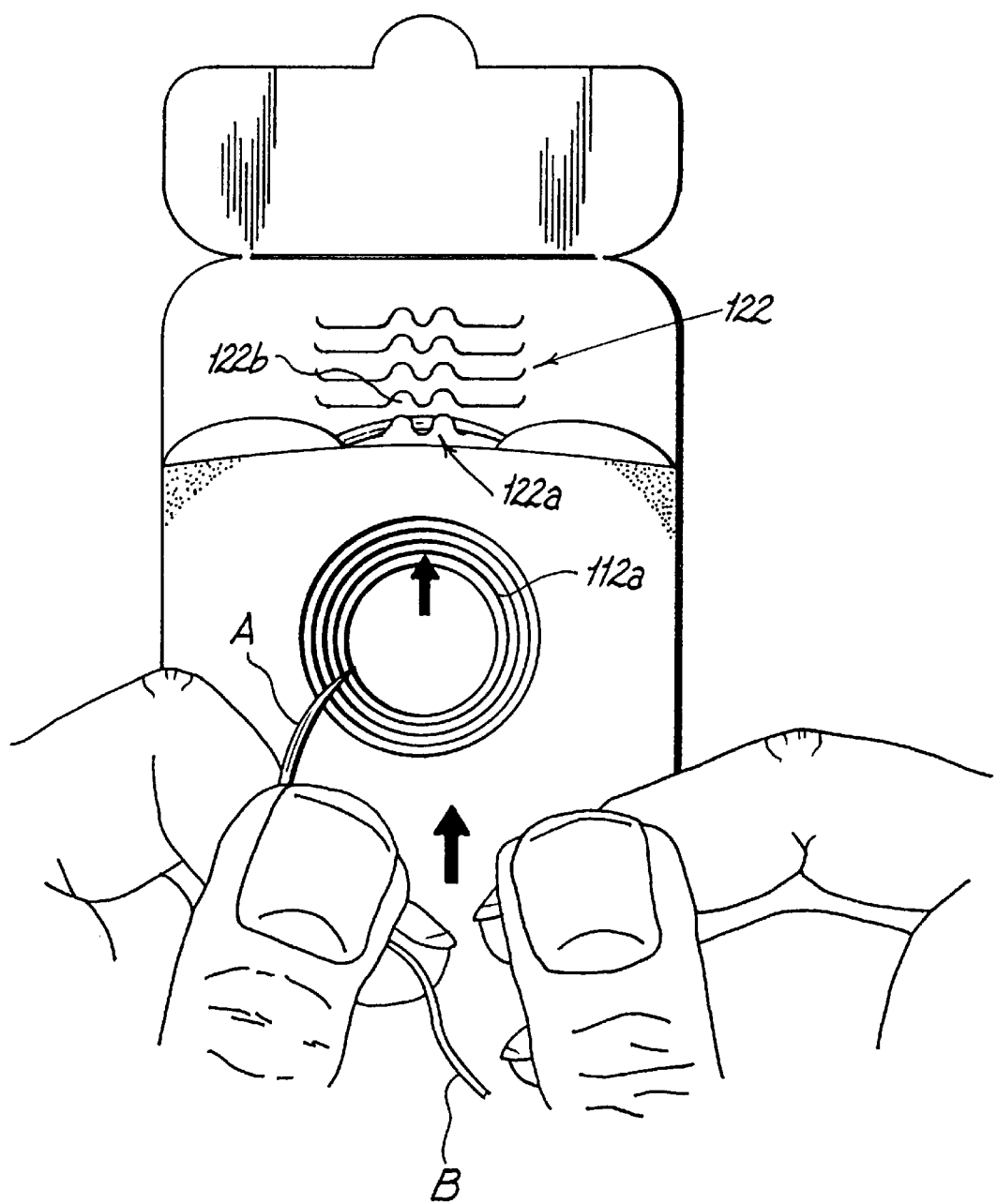

Referring now to FIGS. 4–6, a preferred procedure for loading sutures B with attached needles A within sheet 102 is illustrated. Sheet 102 is folded in the manner shown in FIG. 4 to form five superposed suture compartments with each compartment adapted to retain a flexible suture therein in a coiled configuration. The panels 106–116 are preferably secured in this folded superposed condition prior to positioning on the backing panel. In a preferred embodiment, the superposed panels are secured to each other along their respective peripheries at positions "S" (FIG. 1) by, e.g., sonic welding. Other alternate methods for securing the superposed panels to each other may be readily determined by one skilled in the art such as with the use of adhesives or the like. Once the folded panels of sheet 102 are secured, the sheet is positioned onto backing panel 104 and secured to the backing panel 104 by respective cooperation of the slits 120 of panel 116 and tabs 136 of backing panel 104 (see FIG. 8).

Referring to FIG. 5, a surgical needle "A" having an attached suture B is directed through the front side of the package and positioned under aperture 114a as shown by the indicator arrow. Needle A is then directed through the rear most compartment towards the upper portion of backing panel 104 where it is positioned beneath the first (lowest most) series 122a of alternating cuts 122 to secure needle A to the backing panel 104. Once needle A is secured to backing panel 104, suture B can be fed, either manually or by automation, into the suture compartment defined between panels 114, 116 in a manner such that the suture assumes a coiled configuration within the filament compartment. One method of feeding the suture can comprise pressuring the suture into the retainer while rotating the retainer until the entire suture is disposed within the compartment. It is to be appreciated that the suture tends, under the influence of its resilient qualities, to coil and expand radially outwardly to the peripheral portion of the suture compartment. Accordingly, the suture B is retained in the outer peripheral portions of the compartment.

Referring now to FIG. 6, the loading of package 100 is continued by inserting a second needle A with attached resilient suture B through the front of package 100 and positioning the needle A within aperture 112a as shown by the indicator arrow. Needle A is then directed to the upper portion of backing panel 104 where it is positioned beneath the next set of arcuate tabs 122b of the backing panel. Thereafter, suture B attached to the second needle A is fed into the individual suture compartment defined between panels 112, 114 such that the suture assumes a coiled configuration within the compartment and is fully loaded within the compartment. The remaining needles A with attached resilient sutures B are loaded within the series of needle retaining tabs 122 and remaining suture compartments in the same manner. FIG. 1 depicts a fully loaded suture package with needles A secured within the series of cuts and tabs 122, 124. After loading, the sutures can be sterilized by ethylene oxide, irradiation or other known sterilization methods.

In a preferred method of loading, each armed suture to be loaded can be sequentially passed through their respective suture compartments and placed in their respective retaining tabs. After all needles are in place, all attached sutures B can be simultaneously pressured to assume a coiled configuration in their respective compartments.

In an alternative method of loading, each suture may be wound into a tight coiled configuration and introduced within the appropriate loading aperture whereupon release of the coiled sutures, the sutures, under the influence of their resilient properties, expand outwardly into their respective individual suture compartments. In accordance with this method, the needles A attached to the sutures B are secured to backing panel after the suture is loaded with the individual suture compartment.

Referring still to FIG. 1, once all the needles and sutures are loaded within the package, aperture cover panel 118 is folded to cover apertures 106a–114a and needle protecting panel 130 of backing panel 104 is folded onto the secured needles A. Panel 130 can be secured by positioning Tab 134 beneath front panel member 106. FIG. 7 illustrates package 100 in the completely secured condition. FIG. 9 is a cross-sectional view taken along lines 9—9 of FIG. 7 illustrating the suture compartments with coiled sutures A loaded therein. While the present invention is shown with individual sutures in each compartment, the scope of the invention clearly includes loading of multiple sutures within each compartment.

Figure 11:
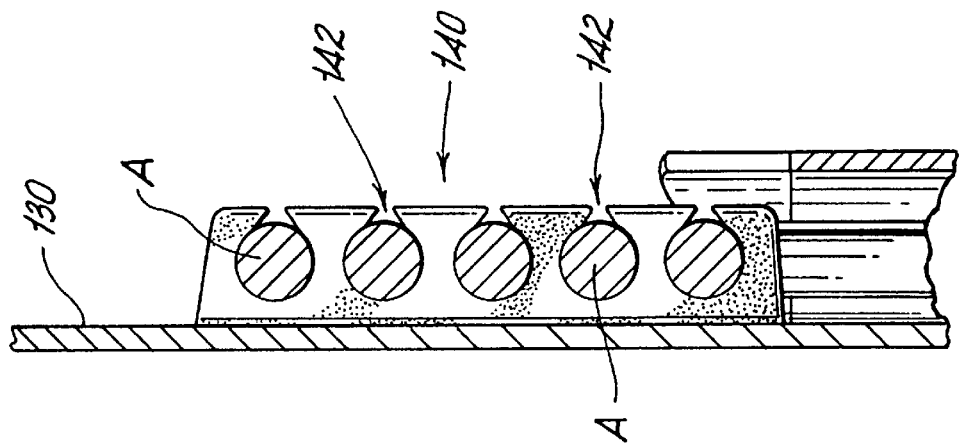
FIG. 11 is a cross-sectional view taken along the lines 11—11 of FIG. 10 illustrating retention of the needles within the foam park.
Figure 10:
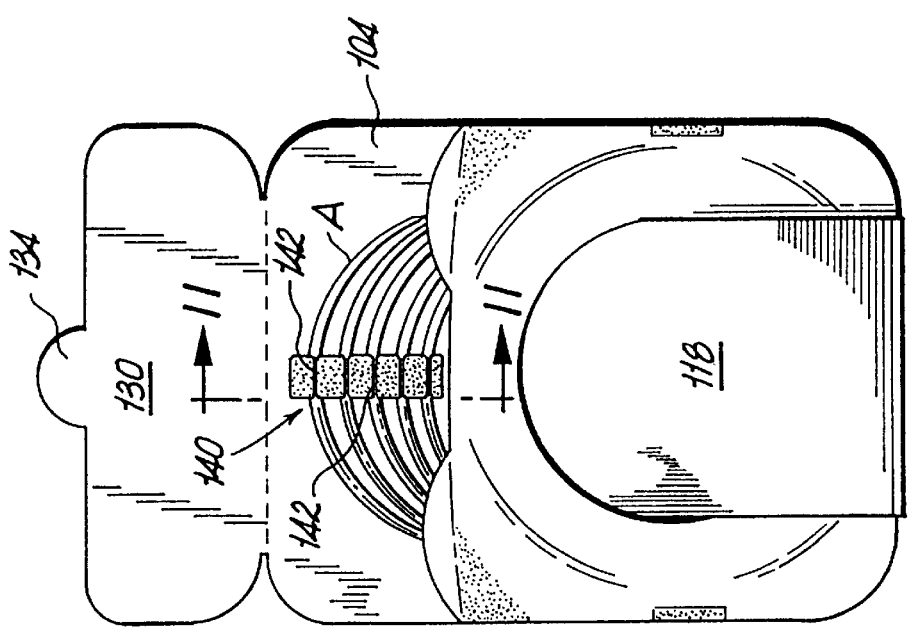
FIG. 10 is a frontal plan view of an alternative embodiment of the suture retainer package of FIG. 1 including a backing panel member having a foam park for retaining the needles.

Referring now to FIGS. 10–11, the package of the present invention is illustrated with an alternative needle park. Backing panel 104 of this embodiment includes a foam needle park 140 which replaces the sinusoidal cut and tab arrangement of the embodiment of FIG. 1 for retaining the needles. Foam needle park 140 includes lateral slits 142 with each slit adapted to accommodate and frictionally engage needles A positioned therein as shown in the cross-section of FIG. 11. Needle protecting panel 130 folds onto backing panel 104 to cover the secured needles A and is retained in the secured position by engagement of locking tab 134 with one of the panel members 104–116.

Figure 13:
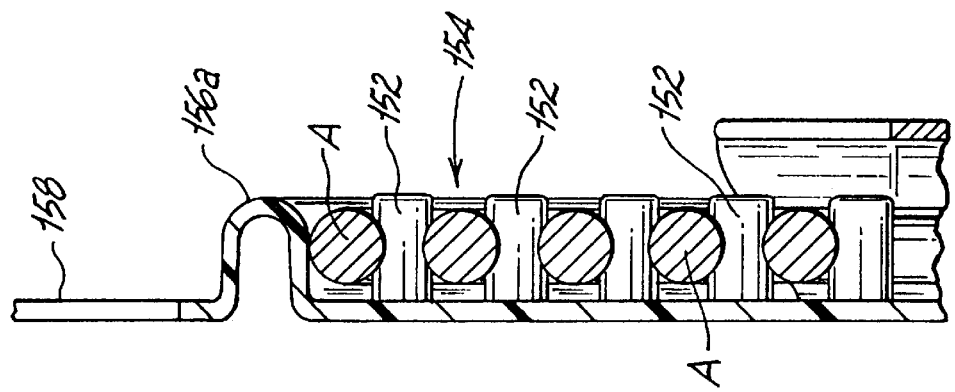
FIG. 13 is a cross-sectional view taken along the lines 13—13 of FIG. 12 illustrating retention of the needles within needle receiving slots defined by the adjacent raised portions.
Figure 12:
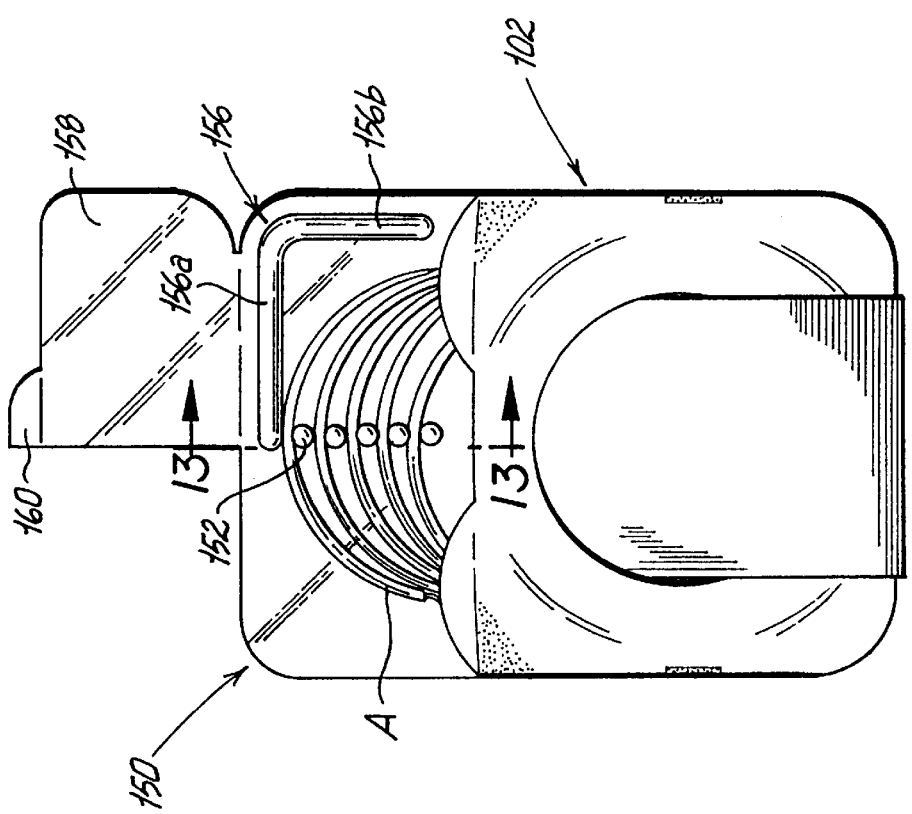
FIG. 12 is a frontal plan view of another alternative embodiment of the suture retainer package of FIG. 1 including a molded plastic backing panel having a plurality of adjacent arcuate raised portions and a needle holding panel for securing the needles.

FIGS. 12–13 illustrate another alternative embodiment of the package of the present invention. Backing panel 150 of this package is preferably formed of molded plastic and includes circular-shaped retaining members 152 extending generally transversely relative to the plane defined by backing panel 150 and integrally formed therewith. The retaining members 152 are advantageously spaced to define needle receiving slots 154 to accommodate the needles A. In particular, an individual needle A is placed within each slot 154 defined between adjacent retaining members 152 and is frictionally engaged by the retaining members 152 on each of the inner and outer curved surfaces of the needle. Retaining members 152 may be deformable such that the retaining surfaces at least partially conform to the outer peripheral dimensions of the needle A. In an alternative embodiment, retaining members 152 may be substantially rigid and may be dimensioned to engage the inner and outer curved surfaces of the needle at a single point on each needle surface. In accordance with this alternative embodiment, the radius of each circular raised portion would be significantly less than the radius of curvature defined by the surgical needle.

Referring still to FIGS. 12–13, backing panel 150 further includes a peripheral rib 156 extending along portions of the upper edge and side edge of the backing panel as shown. The lateral portion 156a of rib 156 and the uppermost retaining member 152 adjacent the upper edge of backing panel 150 define a needle receiving slot to secure a surgical needle A as shown. Rib 156 also supports half needle protecting flap 158 which is folded against the upper portion of backing panel 150 during securement of the package. Half needle protecting flap 158 folds onto the pointed ends of the needles A to assist in retaining the needles A within needle receiving slots 154 defined between retaining members 152. Thus, the combination of retaining members 152, peripheral rib portion 156a and half needle protecting flap 158 secure the needles A to backing panel 150. Needle protecting flap 158 is maintained in the closed folded position by insertion of tab 160 beneath the front most panel member. An alternative method for securing needle protecting flap 158 in the folded closed position is heat sealing the needle protecting flap along peripheral rib 156.

Referring now to FIGS. 14–15 there is illustrated another alternative embodiment of the suture package of the present invention. This package is substantially similar to the package described in the embodiment of FIGS. 12–13 and includes a molded plastic backing panel 170 having transverse retaining members 172. Retaining members 172 are substantially circular in cross-section and include circumferential lip portions 174 (FIG. 15) which overlap the needle receiving slots 176 defined by the adjacent retaining members 172. Lip portions 174 engage the surfaces of the needles A to retain the needles against backing panel 170 and within the needle receiving slots. Peripheral rib 178 extends along the length of upper edge 180 and partially along side edges 182. The transverse portion of peripheral rib 178 and the uppermost retaining member 172 define a needle receiving slot for accommodating a needle A. Needle protecting flap 184 is adapted to fold over to enclose the secured needles A.

To the extent not already indicated, it also will be understood by those of ordinary skill in the art that any one of the various specific embodiments herein described and illustrated may be further modified to incorporate features shown in the other specific embodiments. For example, while armed sutures have been utilized to describe the present invention, the present invention can be used to retain unarmed resilient filaments, wherein one end of the filament can optionally be placed in the aforedescribed "needle park." Furthermore, while the present invention has primarily been described in conjunction with surgical sutures, the package can also be used to accommodate other resilient filaments such as strings for musical instruments. Guitar strings, for example, can be loaded into a retainer having six compartments, one each for the E (low), A, D, G, B, and E (high) strings.

The invention in its broader aspects therefor is not limited to the specific embodiments herein shown and described but departures may be made therefrom within the scope of the accompanying claims without departing from the principles of the invention and without sacrificing its chief advantages. For example, while the present invention has been described in terms of filaments, the invention clearly includes packaging multifilament strands and/or sutures.

What is claimed is:

1. A package for filaments comprising:
   at least four panel members foldably connected to each other along transverse sides thereof and arranged to fold upon each other to form at least three superposed compartments defined between pairs of adjacent panel members, each said compartment having a forward panel member and a rear panel member, each said forward panel member having an aperture formed therein, said apertures being in general concentric alignment with each other such that each said compartment can be accessed from a front side of the retainer package when said panel members are in a folded condition, said apertures generally decreasing in dimension from a front most filament compartment to a rearmost filament compartment to facilitate loading of the filaments within said compartments; and
   at least one filament disposed within each said compartment, wherein each filament in each compartment is separate and distinct from a filament in another compartment.

2. The package according to claim 1, wherein each filament is a surgical suture.

3. The package according to claim 1, wherein each filament is a musical instrument string.

4. The package according to claim 3, wherein three or more musical instrument strings are disposed within the package, each individually disposed within separate filament compartments.

5. The package according to claim 3, wherein each musical instrument string is designed for use with a guitar.

* * * * *